(12) United States Patent
Lowry et al.

(10) Patent No.: US 7,300,421 B1
(45) Date of Patent: Nov. 27, 2007

(54) SAFETY SYRINGE AND SAFETY SYRINGE ADAPTER

(75) Inventors: Suzanne L. Lowry, 11 Highland Park La., Atlanta, GA (US) 30306; Vlad Moise, Marietta, GA (US); Willis Whiteside, Lawrenceville, GA (US)

(73) Assignee: Suzanne L. Lowry, Atlanta, GA (US)

( * ) Notice: Subject to any disclaimer, the term of this patent is extended or adjusted under 35 U.S.C. 154(b) by 889 days.

(21) Appl. No.: 10/304,296

(22) Filed: Nov. 26, 2002

(51) Int. Cl.
*A61M 5/32* (2006.01)
(52) U.S. Cl. .................................................... 604/198
(58) Field of Classification Search ............... 604/111, 604/93.01, 48, 198, 192, 110, 187, 263, 264
See application file for complete search history.

(56) References Cited

U.S. PATENT DOCUMENTS

| | | | |
|---|---|---|---|
| 4,840,185 A | 6/1989 | Hernandez | |
| 4,908,023 A | 3/1990 | Yuen | |
| RE33,585 E | 5/1991 | Haber et al. | |
| 5,300,040 A * | 4/1994 | Martin | 604/198 |
| 5,376,080 A | 12/1994 | Petrussa | |
| 5,591,138 A | 1/1997 | Vaillancourt | |
| 5,685,862 A | 11/1997 | Mahurkar | |
| 5,885,256 A | 3/1999 | Chern et al. | |
| 5,984,899 A | 11/1999 | D'Alessio et al. | |
| 6,106,500 A | 8/2000 | Mahurkar | |
| 6,149,630 A * | 11/2000 | Robinson | 604/198 |
| 6,183,439 B1 | 2/2001 | Nakajima | |
| 6,287,282 B1 | 9/2001 | Bonaldo et al. | |
| 6,976,976 B2 * | 12/2005 | Doyle | 604/198 |
| 2001/0037089 A1 | 11/2001 | Domci, Jr. | |

* cited by examiner

*Primary Examiner*—Nicholas D. Lucchesi
*Assistant Examiner*—Christopher D Koharski
(74) *Attorney, Agent, or Firm*—Seyfarth Shaw LLP

(57) ABSTRACT

The present invention provides for a universal safety syringe adapter that allows for a standard syringe, vacuum tube or other medical device to be quickly modified to have a protective sheath which may be deployed automatically upon activation of a release member with a single hand in order to propel the protective sheath from a retracted position to an extended position covering a needle in order to avoid sharps injuries and protect medical or other professionals using the instrument. The present invention also provides for a syringe safety device which includes a protective sheath having an elastic member in order to propel the protective sheath from a retracted to an extended position.

30 Claims, 6 Drawing Sheets

SAFETY SYRINGE AND SAFETY SYRINGE ADAPTER

The present invention pertains to a universal safety adapter "companion" device, for currently existing syringes, as well as, a modified vacutainer and a safety syringe having an automatically deployed protective sheath.

BACKGROUND

Official figures for sharps injuries (accidental needle or sharp instruments impaling medical or other professionals, who routinely use these devices) are about 800,000 to 1,000,000 reported per year. In light of under-reporting by nurses, physicians and other health care professionals, this number is likely as high as 2 to 3 million per year (in all health care settings). Each year the cost to the medical industry is over $3 billion, for both testing and treating injured health care professionals. Everyday, 9000 health care workers in the United States sustain a disabling injury from sharps (average cost per hospital is greater than $24,000). Average cost per injury is $2500 to $4000. A single sero-conversion of Hepatitis C carries a lifetime cost of greater than $600,000. If the healthcare industry is spending twice the cost (on an injured worker) of the expense to manufacture conventional syringes, it is financially assumable, that safety devices might ultimately be worth the investment. These costs do not even consider the potential legal costs to defend use of a device with no safety mechanism.

In 1999, Federal legislation passed the Needle-stick Safety and Prevention Act, which now requires the OSHA compliance officer to review sharps injuries under the Blood Born Pathogens Standards. This requires employers to establish and maintain a sharps injury log of contaminated sharps which should include: type and brand of device used; department where injury occurred; and explanation of how the incident occurred.

Currently six states have existing needle-stick legislation and many other states have adopted the Federal legislation into their OSHA policies. In February 2000, the obvious legislative interest for improved sharps injury incidence recording was demonstrated by the National Institute of Health grants of $300,000 to improve strategies and methods of detecting and accurately reporting sharps injuries in the health care industry. Additionally OSHA has the authority to levy fines for repeat violations, if facilities fail to have adequate provisions to protect their employees. Regulatory measures regarding all safety devices will likely increase over the next few years secondary to enforced legislation.

Controversy currently exists, with new studies supporting single-use tube holders to avoid contamination with blood during phlebotomy procedures (venous collection of blood). A recent study showed that 83% of randomly selected tube holders showed blood contamination. Simultaneously, "safety syringes" defeat the purpose of the safety design when used for phlebotomy in that, the transfer mechanism to a specimen container introduces an even greater risk to the user. Most sharps injuries are from needle-stick injuries, usually caused by two-handed recapping of the needle after use. Syringes are used in multiple situations: intra-muscular injections, subcutaneous injections, intra-venous (both to administer medications and for phlebotomy), as a support base to place an I.V. catheter and as a direct attachment to I.V. tubing.

Needles are disposed in a specific container designed to be sealed after being filled with sharps. However, there is no standard practice in place for filling the containers. Containers are often irregularly filled with sharps attached to syringes, scalpel blades, lancets and anything deemed appropriate by the health care worker using the container. Needles are often seen protruding through the opening in over-filled containers. This practice, poses a risk to the bio-hazards disposal workers. Needle destruction devices are currently available. Utilization of these devices remains hazardous, as the risk of needle-stick still exists during transport to the device (regardless of destruction of the needle). Much of I.V. therapy is now done with needless systems. However, regardless of needle-less access, the patient has to initially be impaled to acquire the I.V. placement and this requires a needle. Obviously, the same is true of phlebotomy.

The market for syringe/vacutainer devices is thought to be greater than the 12 billion units (worldwide noted in 1996). 85% (approximately 4-5 billion units), of the U.S. market today, continues to be conventional devices (no safety feature). Safety devices (all types), are involved in approximately 15% of the U.S. market today but, evolving legislation will impose a market potential in the next few years of over 10 billion units (if 70-80% of the market demand is met). Currently there are several syringe and needle shields on the market, which claim safety for the intended user. These devices have had some impact on the industry, but continue to be limited because: they require manual intervention, are clumsy (the operator's hand always indirectly approaches the needle), are inconvenient, are not user-obvious, and/or their cost to manufacture is much greater than conventional syringes.

The market has moved slowly in the past, as hospital costs have been scrutinized and controlled by the managed care insurance industry. With legislation now in place imposing liability for the insurance industry, those issues will likely have to be reevaluated in the future. To replace conventional syringes would mean that over 5 billion units already in circulation in the medical, dental and veterinary industry, would likely be recalled (at best) or continue to be used, with the potential risk to the user and liability to the manufacturer.

The ideal solution for the industry would be a product that is easily removed from the sterile packing, is user-obvious, is automatic with single-handed operation, completely encloses the needle after use and locks in place and does not interfere with conventional syringe parameters: clear, easy to read calibrations, any needle size can be used or changed as needed (needle is separate), and is efficiently manufactured, assembled and cost competitive.

The present invention provides for an innovative device which compliments existing technology in that it has the capability of "standing alone" or converting a conventional syringe into a safe, reliable, convenient, automated, single touch, price and assembly competitive, safety syringe. The design allows for prefilled syringes to be converted to safety syringes and when used with an I.V. catheter, it converts routine placement to a safe procedure. The product benefits include: automatic mechanism, fail-proof safety, single handed, user-obvious device, with a low cost to produce. The invention may be used for phlebotomy stations, hospitals, dental, medical and veterinary clinics, physician offices, teaching and research facilities, as well as pre-filled and non-automated existing syringe manufacturer markets.

SUMMARY OF THE INVENTION

In order to provide an invention that overcomes the above disadvantages of the prior art there is provided a syringe safety adapter comprising a barrel adapter including a first end having a syringe mounted to the barrel adapter. A protective sheath is provided including an attachment member, an interior finger and a cylindrical bore for receiving the barrel adapter therein. An elastic member is attached to the interior finger of the protector sheath. A release member is engaged with the attachment member when the protective sheath is in a retracted position providing the elastic member under tension so that upon disengagement of the release member from the attachment member the elastic member will propel the protective sheath from the retracted position surrounding the barrel adapter to an extended position surrounding the needle. In an embodiment the release member may include a resilient tab engaged within an aperture of the attachment member so that upon depression of the release member the tab is removed from the aperture and the elastic member pulls the protective sheath to the extended position. In an embodiment the barrel adapter and the protective sheath may be transparent and calibration indicia of the syringe mounted therein can be identified. In an embodiment, a minimum volume can be identified through the barrel adapter and the protective sheath when the sheath is in either the retracted or extended position.

In an embodiment, the syringe may include a finger plate and the barrel adapter includes an attachment base having a pair of tabs to resiliently capture a finger plate of the syringe between each tab. In an embodiment each tab includes a detente to latch over an edge of the finger plate when mounted between each tab. In an embodiment the elastic member may be a band having a cylindrical hub having attached a pair of extended loops. In an embodiment the hub may fit over the needle and each loop attaches to the interior finger. In an embodiment the loops may be attached to the interior finger and the second end engages the hub so that the loops are stretched to provide an elastic force.

In a further embodiment, a one-hand releasable safety adapter assembly is provided comprising an adapter including a first end having an attachment base and a second end having a spring member extending therefrom. A protective sheath is provided having an aperture for receiving the adapter therein. A release member is provided by the adapter and releasably attached to the protective sheath so that the spring member is under tension. A standard size medical device is mounted to the attachment base providing the adapter assembly wherein the assembly may be held in a single hand while providing for manipulation of the release member with the hand in order to release the protective sheath and propel the protective sheath from a retracted position to an extended position. In an embodiment, the medical device may include a syringe. In an embodiment, the medical device may be a standard one and one-half inch syringe. In an embodiment, the medical device may include a vacuum tube. In an embodiment the medical device may include a catheter.

In an embodiment, the spring member is an elastic member that may be stretched between the first and the second end in order to create sufficient force to propel the protective sheath to the extended position when the protective sheath is released from the release member. In an embodiment a pair of release members may be provided each having a tab engaged with a pair of apertures formed in the protective sheath and the elastic member is attached to an interior of the protective sheath.

In an embodiment, the elastic member may include a first end attached to the interior finger and an engagement portion for receiving the second end and upon insertion of the adapter within the protective sheath the second end of the adapter may move away from the interior finger and stretch the elastic member therebetween until the release member engages an aperture of the protective sheath to retain the protective sheath in a retracted position with the elastic member under tension. In an embodiment, the engagement portion is formed by a second end of the elastic member. In an embodiment, the engagement portion is formed approximately midway between the first end and a second end of the elastic member. In an embodiment, the engagement portion includes a cylindrical hub formed within the elastic member having a loop on each side providing the first and second ends. In an embodiment, the elastic member is a band and the engagement portion includes the two parallel sides of the band intermediate the first end and second end of the band. In an embodiment, the second end of the adapter includes a detente for engaging the sides of the band. In an embodiment, the sides form a cylindrical hub having a loop on each side providing the first end and a second end of the band.

In another embodiment, a method of preventing pin sticks from a needle is provided, comprising the steps of holding a medical device having a needle protruding from a first end in a hand gripping primarily a second end of the medical device, attaching the device to an adapter having a protective sheath mounted to the adapter in a retracted position and retained in the retracted position by a release member, activating the release member with said hand in order to release the protective sheath mounted under tension by an elastic member attached to the protective sheath and to automatically move the sheath to an extended position surrounding the needle. In an embodiment, the method may comprise the steps of grasping a pair of release members between a finger and thumb of the hand and squeezing in order to release the protective sheath and propel the sheath to the extended position. In an embodiment, the method may further comprise the steps of attaching a finger plate of the medical device to an attachment base of the adapter. In an embodiment, the method may comprise the steps of providing the attachment base with a pair of tabs and resiliently capturing the finger plate between the tabs in order to mount the medical device to the adapter.

BRIEF DESCRIPTION OF THE DRAWINGS

For the purpose of facilitating an understanding of the subject matter sought to be perturbed, there are illustrated in the accompanying drawings, embodiments thereof, from an inspection of which, one considered in connection with the following description, the subject matter sought to be protected, its construction and operation, and many of its advantages should be readily understood.

DETAILED DESCRIPTION OF A PRESENTLY PREFERRED EMBODIMENT

Figure 5:
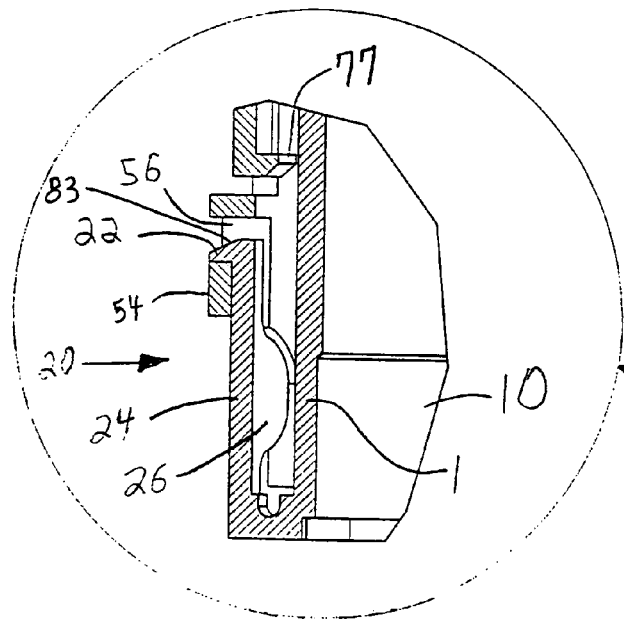
FIG. 5 is an enlarged view of a segment of FIG. 4 identified by circle 5.
Figure 4:
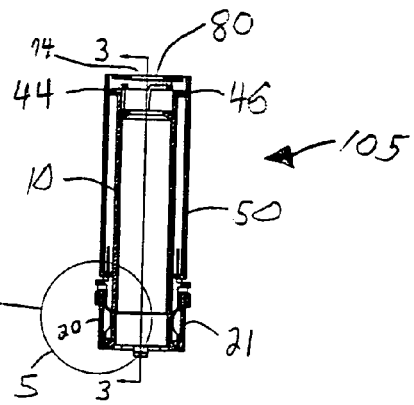
FIG. 4 is a side elevation, cut-away view of FIG. 3 taken at line 4-4.

The present invention is best understood with respect to a description of preferred embodiments disclosed in FIGS. 1-14. A syringe safety adapter assembly 5 is disclosed in FIGS. 1 and 6-9 having a barrel adapter 10 forming a cylindrical aperture 12 and having a first end 14 and a second end 16. A release member 20 is provided at the first end of the barrel adapter. The release member 20 includes a nub 22 protruding from the terminal portion of an arm 24 which includes a spring member 26 (see FIG. 5). An attachment base 28 is provided at the first end 14 of the barrel adapter 10. In an embodiment, the attachment base 28 generally has a diamond shape and includes a recess 30 formed in the base for receiving a syringe therein. In a preferred embodiment the release member 20 has a proximal end by which it is attached to the attachment base 28. At the edges of the recess 30 a pair of tabs 32, 34 are provided each having a pair of detentes 36, 38 for grippingly receiving a syringe therebetween. At the second end 16 of the barrel adapter 10 is provided extension lock which include stop abutments 40, 42 and stop protrusions 44, 46. Running longitudinally along the length of the barrel adapter 10 are guide rails 48, 49.

A protective sheath 50 forms a cylindrical bore 52 for receiving the barrel adapter 10 therein. The protective sheath 50 includes attachment members 54, 55. Formed in the attachment members 54, 55 are apertures 56, 57. Interior fingers 58, 59 are provided protruding from the interior walls of the protective sheath 50. Guide rails 60, 61 run longitudinally along the length of the protective sheath 50 and correspond to the guide rails 48, 49 of the adapter 10 so that the adapter 10 may slide within the cylindrical bore 52 and maintain an axial alignment. Resilient lock tabs 62, 64 (see FIG. 1*a*) are provided at the first end 66 of the protective sheath 50. A second end 68 of the protective sheath 50 includes a hole 74 (see FIG. 2). The sheath 50 includes a pair of lips 76, 77 protruding into the bore 52.

An elastic member 80 is provided having an engagement portion 82 formed between a first end 84 and second end 86. In an embodiment the engagement portion 82 may be a cylindrical hub having loops 90, 92 formed on each side or in an alternate embodiment the engagement portion 82 is provided by the two parallel sides 94, 96 of the portion intermediate the first end 84 and second end 86. In an embodiment, the elastic member 80 may be a rubber band. In an alternate embodiment, the elastic member 80 may be a spring member, for example, a coil spring or other substrate that may recoil, such as a rubber O-ring.

A syringe 100 is provided that in an embodiment, may be a standard one and a half inch syringe. However, the adapter 10 of the present invention may also be formed to receive a vacuum tube, a catheter or any other medical device needing to be modified in order to have a protective sheath 50 attached thereto. The syringe 100 includes a finger plate 102 and a needle 104 having a first length. In an embodiment, the needle 104 may be an independent component that may be attached to an end of the syringe barrel 100 via mechanical means, for example a luer lock.

An assembly method of the syringe safety adapter assembly 5 is described as follows: The elastic member 80 is inserted within the cylindrical bore 52 of the protective sheath 50 by looping the first end and second end 84, 86 around the fingers 59, 58, respectively, protruding within the cylindrical bore 52. The engagement portion 82 of the elastic member 80 is left to float freely within the cylindrical bore 52. The barrel adapter 10 is then inserted within the cylindrical bore 52 of the protective sheath 50 so that its second end 16 is received within the cylindrical bore 52 so that the guide rails 48, 49 align with and receive therein corresponding guide rails 60 or 61. The barrel adapter 10 is slid all the way through the cylindrical bore 52 of the protective sheath 50 until the first end 14 of the barrel adapter 10 is adjacent the first end 66 of the protective sheath 50. In such an orientation, the protective sheath 50 is in a retracted position and a gripping member such as a notch 103*a, b, c, d*, at the second end 16 of the barrel adapter 10 (see FIG. 1*b*) engages the engagement portion 82 of the elastic member 80; stretching the elastic member 80 to an extended position and adding tension to the elastic member 80. In a preferred embodiment a rubber band may be used having 0.060 inch square cross section and approximately 1.5 I.D. In an embodiment the rubber band 80 is made of EPDM 65130 or 65120 rubber and provides for a resistance force of 0.025-1.75 pounds and having an elongation of approximately 25%. In the retracted position (as shown in FIGS. 2-7), the attachment members 54, 55 of the protective sheath engage the release members 20, 21 of the barrel adapter 10. As the barrel adapter 10 is slid into the cylindrical bore 52, a ramped portion 83 of the nubs 22 on the release member 20 will engage the inner sides of the attachment members 54, 55 in order to depress the arm 24 so that the nub 22 can slide past, until the nubs 22 are located over the aperture 56. Upon further insertion, the nub 22 will be received within the aperture 56 in order to lock the attachment members 54, 55 to the release members 20 (see FIG. 5). Therefore, what has been described is an assembly of the barrel adapter 10 to the protective sheath 50 providing the elastic member 80 under tension with the protective sheath 50 in a retracted position. In an embodiment, it is this adapter sheath assembly 105 (see FIGS. 2-4) that can be provided to hospitals or other health agencies or even factories providing medical equipment in order to be assembled to or retro-fit standardized medical devices such as syringes. Such a universal adapter sheath assembly 105 can be used to modify existing devices in the field.

Figure 1:
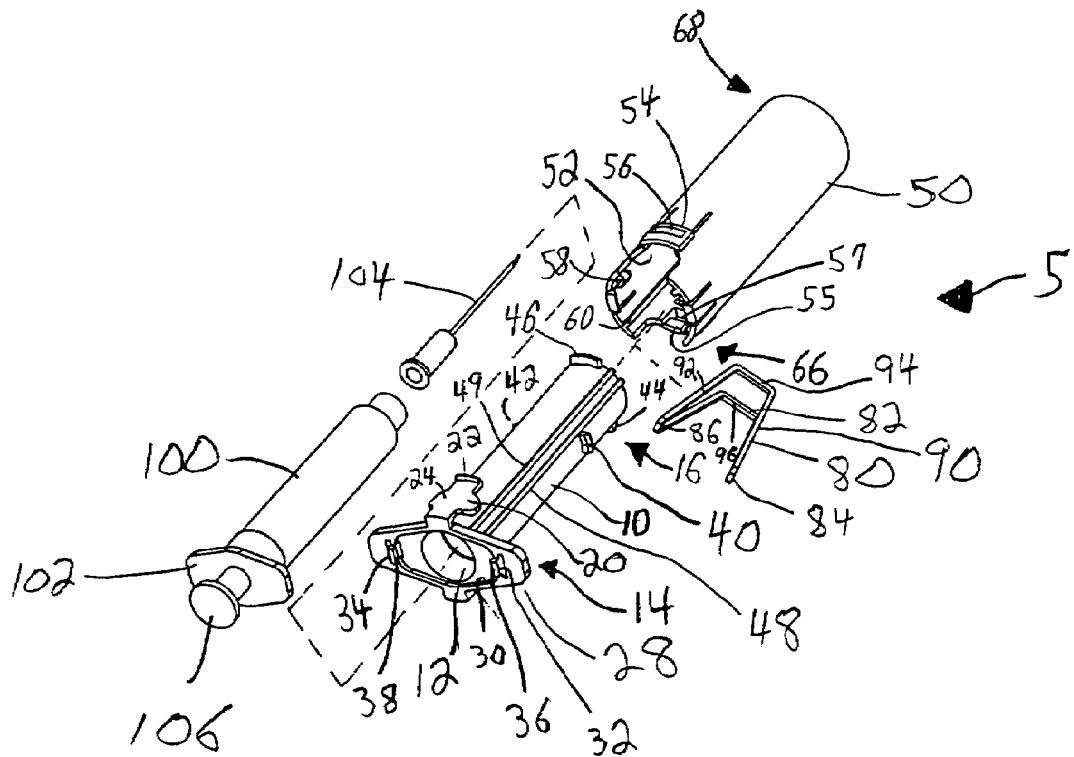
FIG. 1 is an exploded perspective view of the syringe safety adapter assembly of the present invention.
Figure 1A:
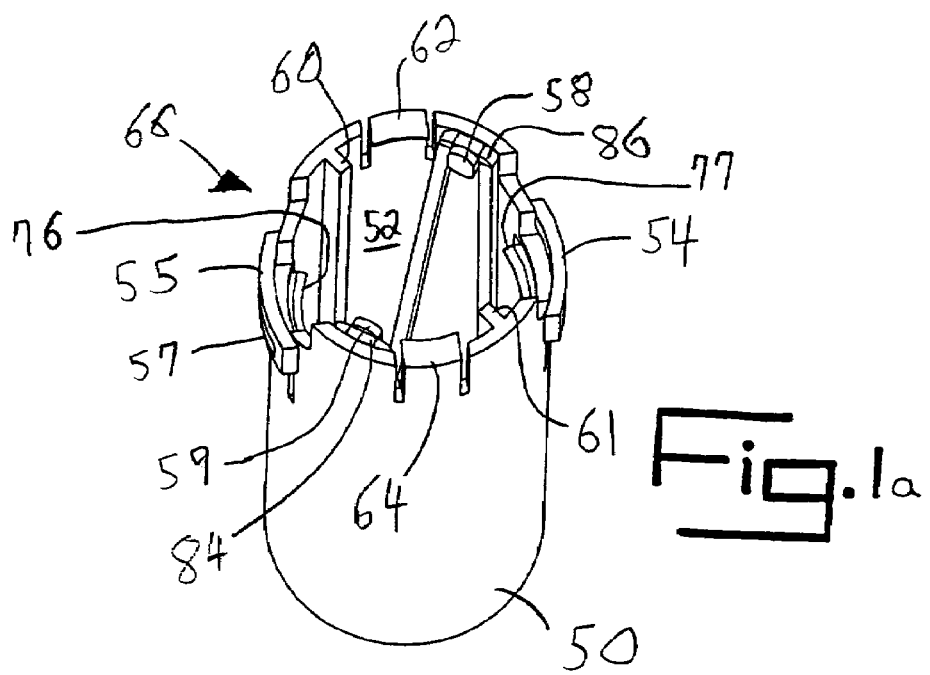
FIG. 1*a* is an enlarged perspective view of the protective sheath of FIG. 1.
Figure 1B:
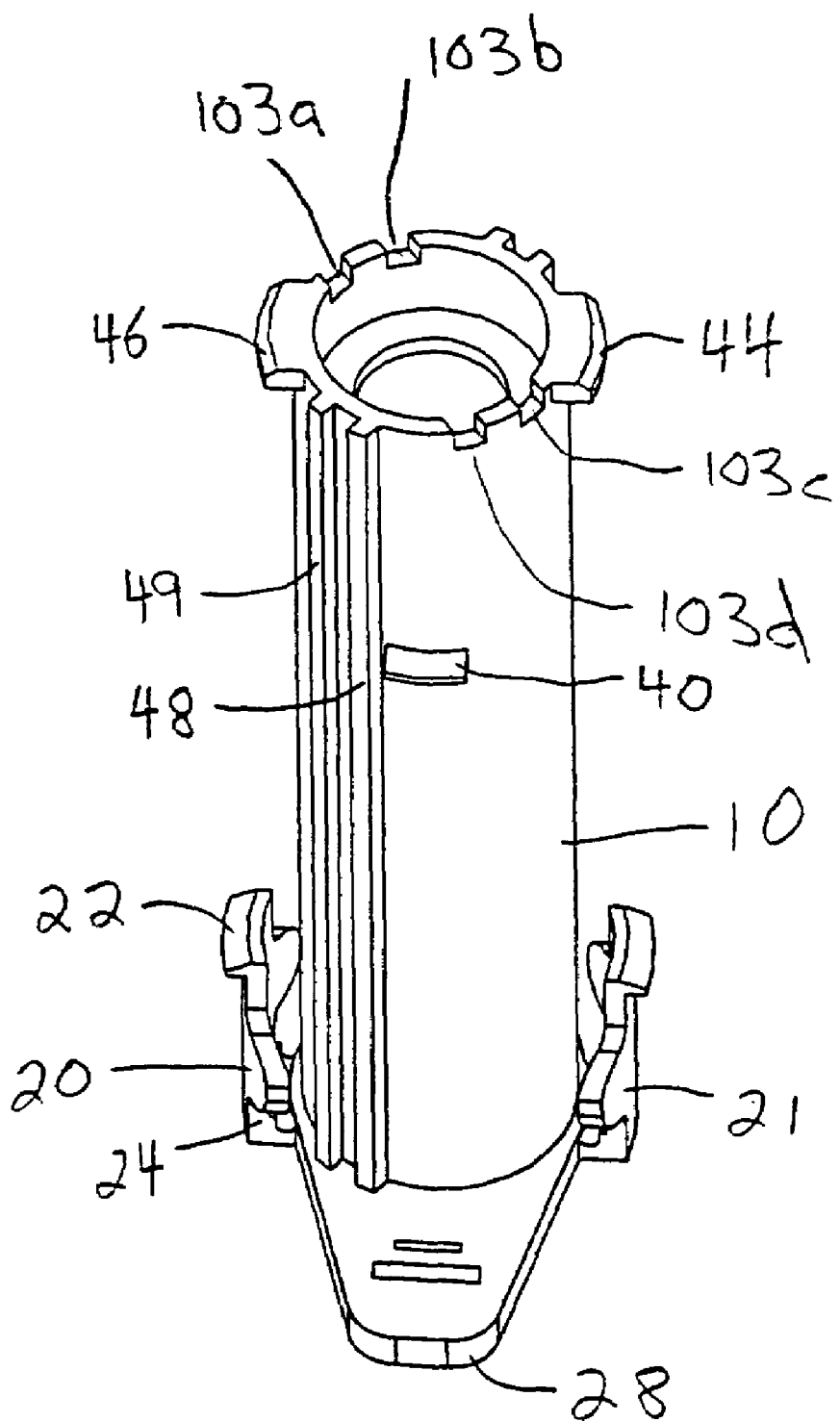
FIG. 1*b* is an enlarged perspective view of the barrel adapter of FIG. 1.
Figure 2:
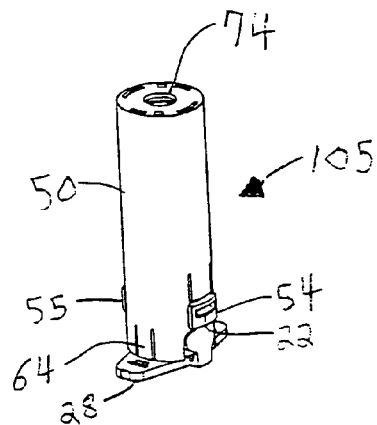
FIG. 2 is a perspective view of a syringe safety adapter of the present invention.
Figure 3:
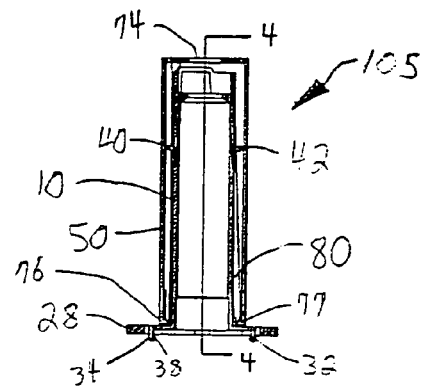
FIG. 3 is a side elevation, cut-away view of FIG. 2 and also of FIG. 4 taken at line 3-3.
Figure 6:
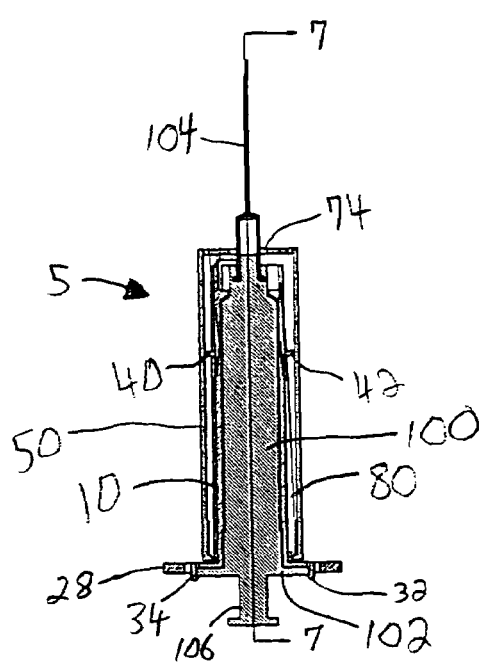
FIG. 6 is a side elevation cut-away view of the assembly of FIG. 1 in an assembled state and a cut away of FIG. 7 taken at line 7-7.
Figure 7:
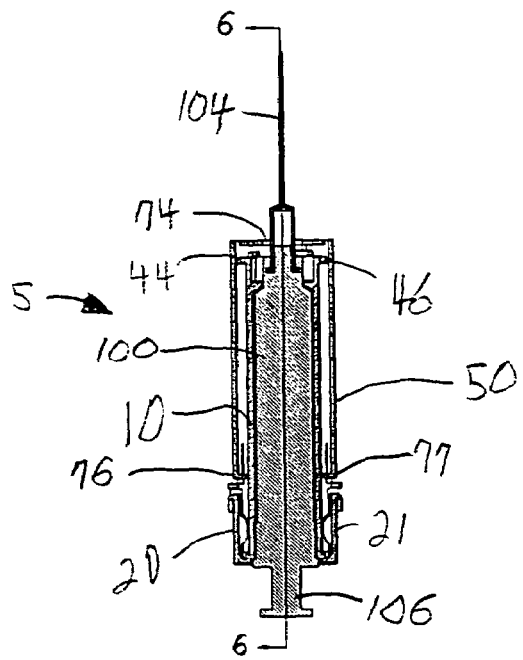
FIG. 7 is a side elevation cut away view of FIG. 6 taken at line 6-6.

As shown in FIG. 1, a standard syringe 100 may be inserted within the barrel adapter 10 so that the needle 104 is inserted through the cylindrical aperture 12 so that it protrudes out the second end 16 and through hole 74 of the protective sheath 50 (see FIGS. 6-7). Upon complete mating of the syringe 100 within the barrel adapter 10, the finger plate 102 is received between the tabs 32, 34 on the attachment base 28 of the barrel adapter 10. The detentes 36, 38 of the tabs 32, 34 grip the edges of the finger plate 102 so that it cannot be easily removed from the attachment base 28. When the protective sheath 50 is in the retracted position as shown in FIGS. 2-7 the syringe may be operated in its normal fashion by inserting the needle 104 into a patient or a bottle or other apparatus and withdrawing fluid with a plunger 106. Then a patient may be inserted with the liquid or have blood drawn from the patient.

Figure 8:
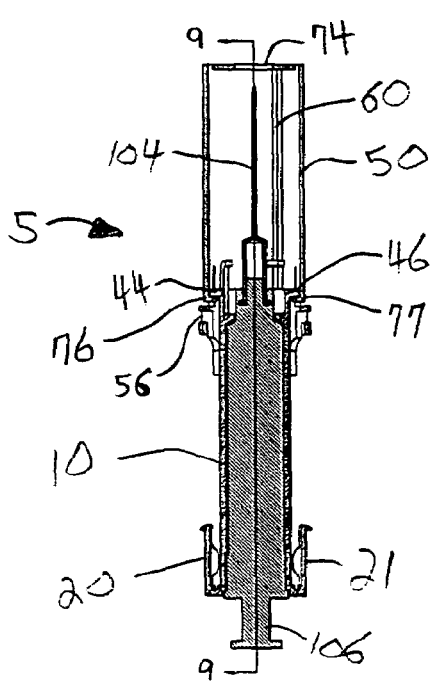
FIG. 8 is a side elevation cut away view of FIG. 7 in an extended position and a side elevation cut-away view of FIG. 9 taken at line 8-8.
Figure 9:
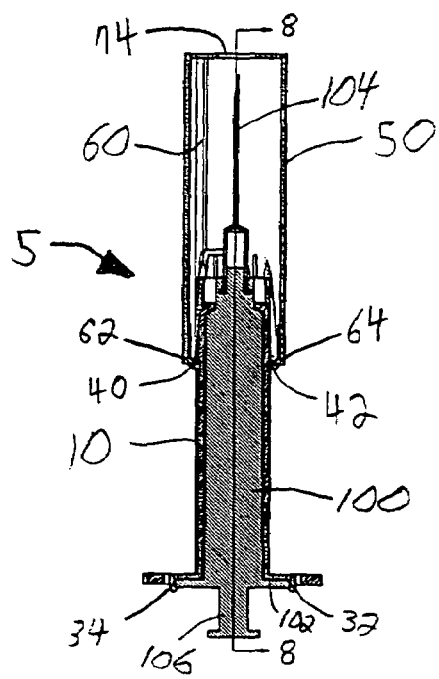
FIG. 9 is a side elevation cut-away view of FIG. 8 taken at line 9-9.

After operation of the syringe 100, the protective sheath 50 may be automatically moved to an extended position covering the needle 104 by depressing the release members 20, 21 in order to release the protective sheath 50 from its retracted position. The release members 20, 21, in an embodiment may be squeezed between a finger and a thumb of an operators hand, so that the arm 24 is depressed and the spring member 26 abuts against the wall 108 of the adapter 10 (see FIG. 5). The arm 24 may pivot within the aperture 56 sufficiently to allow the nub 22 to exit the aperture 56 and slide past the attachment member 54, freeing the sheath 50 from adapter 10 in a retracted position and allowing the elastic member 80 to pull the protective sheath 50 toward the second end 16 of the barrel adapter 10. Because the elastic member 80 first and second ends 84, 86 are under tension, they will pull on the fingers 58, 59 of the sheath 50 and propel the sheath along the adapter 10 in a linear ascension toward the first end 16 to an extended position surrounding the needle 104 (as shown in FIG. 8 and FIG. 9). The protective sheath 50 is locked in the extended position by the locking tabs 62, 64 sliding past and engaging the stop abutments 40, 42 on the barrel adapter 10. The locking tabs 62, 64 have ramped surfaces that engage the stop abutments 40, 42 causing the locking tabs 62, 64 to expand so that they can slide past and retract to lock against the stop abutments 40, 42 (as shown in FIG. 9). Therefore, once the protective sheath 50 has been activated and moved to its extended position it cannot be moved back down to the retracted position without great difficulty. As well, the sheath 50 is prevented from sliding too far and off of the adapter 10 by stop protrusions 44, 46 engaging lips 76, 77 of the sheath 50. Due to the guide rails 48, 49, 60, 61 the adapter 10 and sheath 50 maintain an axial alignment so that upon propulsion of the sheath 50 the locking tabs 62, 64 stay aligned with the stop abutments 40, 42 and lips 76, 77, respectively.

Figure 10:
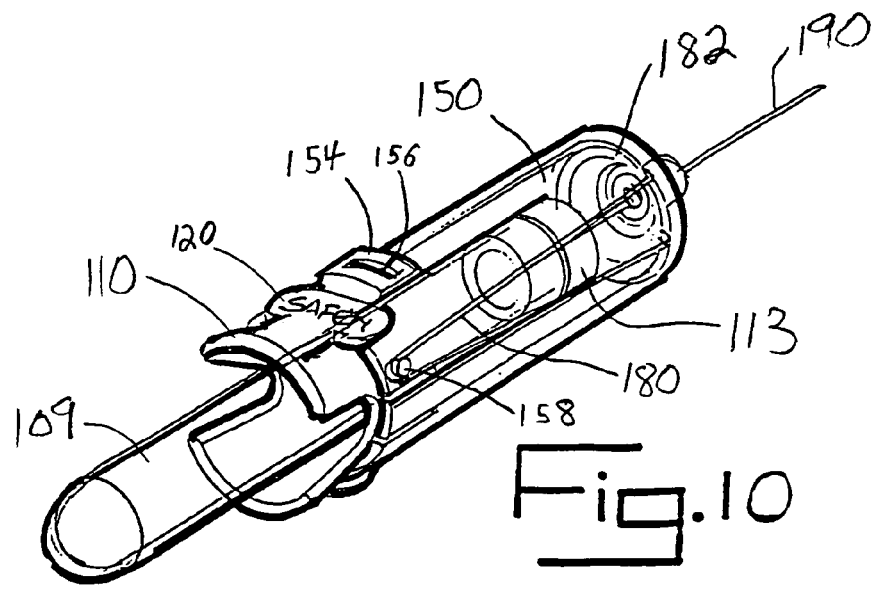
FIG. 10 is a perspective view of a further embodiment of the invention.
Figure 11:
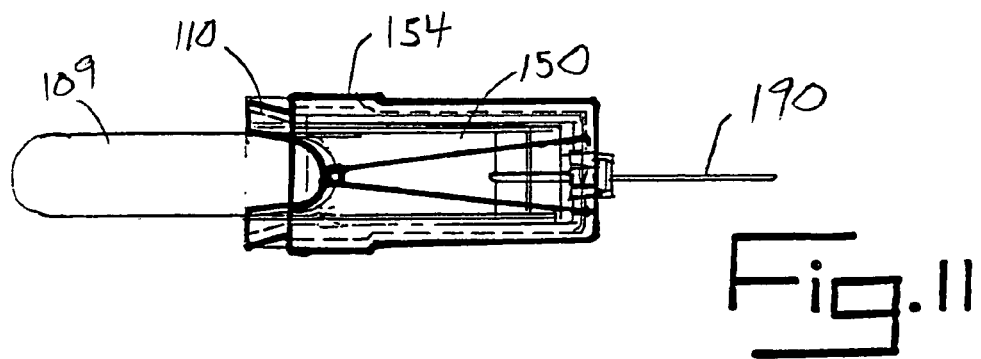
FIG. 11 is a side elevation view of the invention of FIG. 10 in a retracted position.
Figure 12:
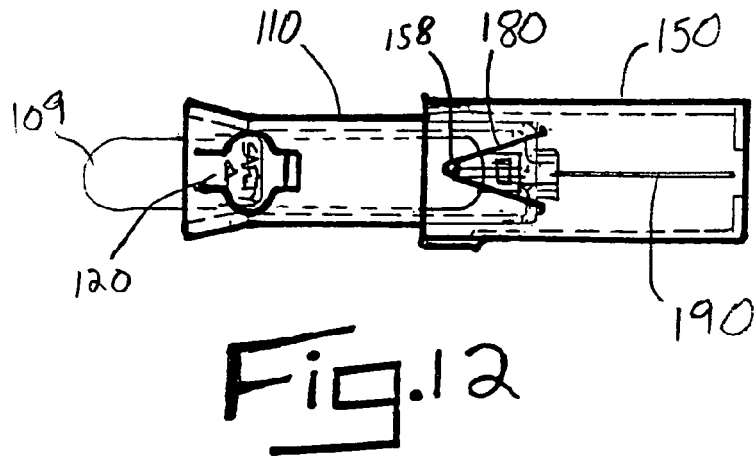
FIG. 12 is a side elevation of FIG. 11 in an extended position.

An additional embodiment of the invention is shown in FIGS. 10-12 disclosing a safety adapter assembly for a vacuum tube or vacutainer device 109. The vacuum tube may be of any standard size. The vacuum tube is received within a barrel adapter 110 which includes a retention means 113 for grippingly holding the vacuum tube 109 within the aperture of the barrel adapter 110. Protruding from the barrel adapter 110 is a release member 120 which is received by a protective sheath 150 having an attachment member 154 with an aperture 156. The release member 120 operates as discussed above for the syringe adapter sheath 105 embodiment.

In the retracted position as shown in FIG. 10, the release member 120 is inserted within the aperture 156 of the attachment member 154. In the retracted position a finger 158 grasps onto an end of the elastic member 180 which is stretched around the second end 182 of the barrel adapter 110. A needle 190 protrudes from the end of the protective sheath 150. Upon release of the release member 120, the protective sheath 150 may move toward the second end 182 propelling the protective sheath 152 to an extended position as shown in FIG. 12. In the extended position, the elastic member 180 is relaxed and the needle 190 is enclosed by the protective sheath 150. Stop abutment members, as described previously, prevent the protective sheath 150 from moving back to the retracted position over the barrel adapter 110.

Therefore, it may be understood that a standard vacuum tube may be quickly and easily modified with the barrel adapter 110 attached thereto in order to provide a safety system to cover the needle 190 after use of the vacuum tube 109.

Figure 13:
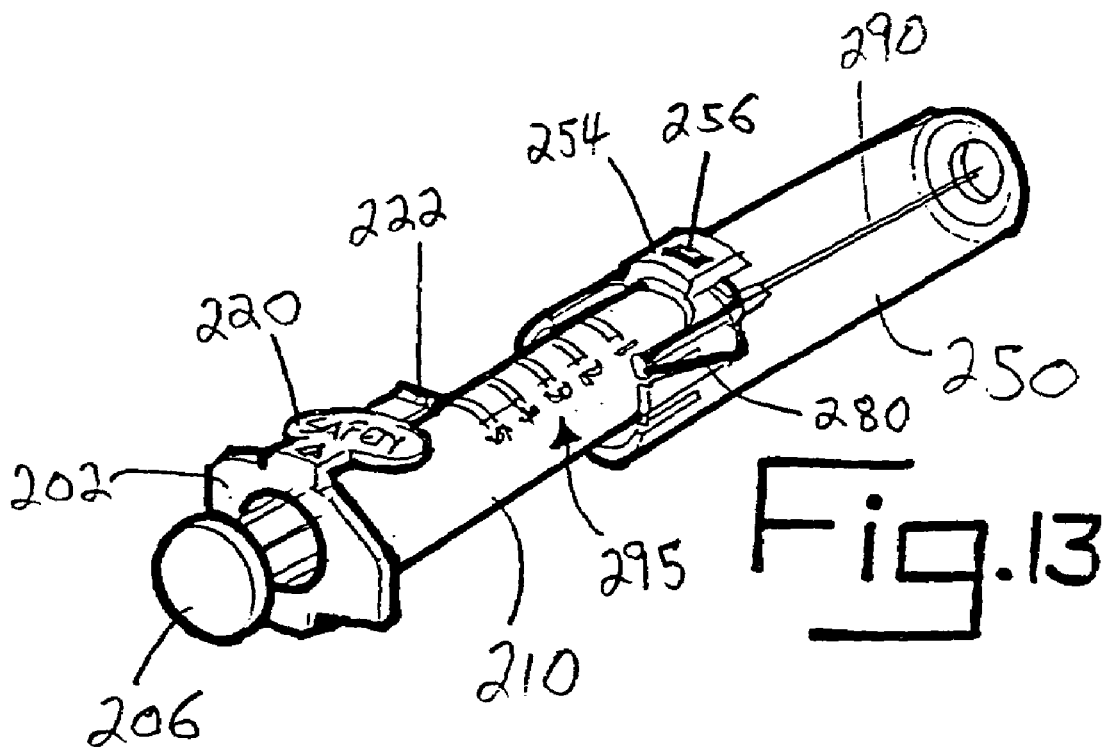
FIG. 13 is a perspective view of a further embodiment of the invention in an extended position.
Figure 14:
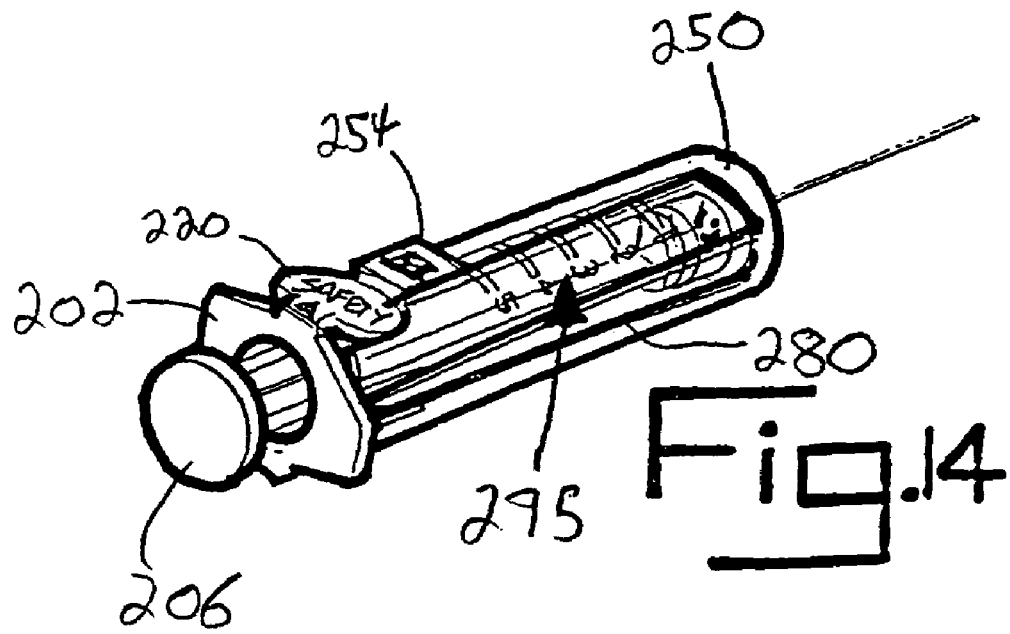
FIG. 14 is a perspective view of the invention of FIG. 13 in a retracted position.

In a further embodiment of the present invention, there is provided a safety syringe as shown in FIGS. 13 and 14. In this embodiment, a standard syringe is modified to provide a barrel 210 having a finger plate 202 and a plunger 206 received within the aperture of the barrel 210. A release member 220 is attached to the finger plate 202. In an embodiment, the entire barrel 210 is injection molded of a polymer material having the finger plate 202 and the release member 220 integrally formed. At the distal end of the release member 220 is a nub 222. The barrel 210 is slid within protective sheath 250, as discussed above, so that the nub 222 engages the attachment member 254 by being inserted within the aperture 256, in order to lock the protective sheath 250 in a retracted position as shown in FIG. 14. An elastic member 280 is mounted within the interior of the protective sheath 50, as discussed above, so that when the protective sheath 250 is moved down to its retracted position the elastic member 280 will stretch so that it is under tension. Upon depression of the release member 220 the protective sheath is released in order to cover a needle 290.

As shown in FIG. 13, the barrel 210 includes measurement indicia 295 such as "1-5 cc." In an embodiment, both the barrel 210 and the protective sheath 250 are formed of a transparent material, such as clear plastic, which allows for the measurement indicia 295 to be viewed when the safety syringe assembly is in either the retracted or extended position. Therefore, it may be understood that a standard size syringe may be formed having the additional feature of a release member 220 attached thereto. By addition of this single member, a protective sheath 250 may be attached thereto in order to provide a syringe with a safety feature for protection of the needle 290 after use of the syringe. It also may be understood that while a standard syringe may not be adapted in the field as is provided by the embodiment shown in FIGS. 1-9, one less piece is needed for the present embodiment of FIGS. 13-14; and such a syringe can be inexpensively manufactured. In addition, in an embodiment the barrel 210 and protective sheath 250 may include stop abutments, as discussed above, in order to maintain the protective sheath 250 in its extended position as shown in FIG. 13 so that it cannot be retracted.

The matter set forth in the foregoing description and accompanying drawings by way of illustration only not as a limitation. While particular embodiments have been shown and described, it would be obvious to those skilled in the art that changes and modifications may be made without departing from the broader aspects of applicant's contribution. The actual scope of the protection sought is intended to be defined in the following claims when viewed in their proper perspective based on the prior art.

What is claimed is:

1. A safety sheath assembly comprising:
 a barrel adapter for attaching a syringe without impeding full movement of a plunger reciprocating within the syringe;
 a protective sheath including an attachment member, an a pair of interior fingers and a cylindrical bore for receiving the barrel therein;
 an elastic band attached to the pair of interior fingers of the protective sheath, the elastic band is a single continuous member having an engagement portion attached to a pair of extended loops; and the engagement portion fits over a needle of a syringe mounted therein and each loop attaches to the pair of interior fingers; and a release member engaged with the attachment member when the protective sheath is in a retracted position providing the elastic band under tension so that upon disengagement of the release member from the attachment member the elastic band will pull the protective sheath from the retracted position surrounding the barrel to an extended position.

2. The assembly of claim 1 wherein the release member includes a nub engaged within an aperture of the attachment member so that upon depression of the release member the nub is removed from the aperture and the elastic band pulls the protective sheath to the extended position.

3. The assembly of claim 1 wherein the barrel adapter and the protective sheath are transparent and calibration indicia of a syringe mounted therein can be identified.

4. The assembly of claim 3 wherein the indicia for a minimum volume can be identified through the barrel and the protective sheath when the sheath is in either the retracted or extended position.

5. The assembly of claim 3 wherein the syringe includes a finger plate and the barrel includes an attachment base having a pair of tabs to resiliently capture the finger plate of the syringe between each tab.

6. The assembly of claim 5 wherein each tab includes a detente to latch over an edge of the finger plate when mounted between each tab.

7. The assembly of claim 1 wherein the elastic band is a rubber band having an engagement portion attached to a pair of extended loops.

8. The assembly of claim 7 wherein the engagement portion fits over a top end of a needle of a syringe mounted therein and each loop attaches to the interior finger.

9. The assembly of claim 8 wherein the loops, when attached to the interior finger and the second end engages the engagement portion, the loops are stretched to provide an elastic force of at least 0.075 pounds.

10. The assembly of claim 1 wherein the barrel adapter includes a first end having a syringe mounted to the barrel adapter, the syringe including a needle having a first length and the protective sheath equal to or longer than the first length.

11. The assembly of claim 1 wherein the barrel adapter includes an attachment plate and the release member protrudes therefrom.

12. The assembly of claim 1 wherein the barrel includes a stop abutment for maintaining the protective sheath in the extended position.

13. The assembly of claim 1 wherein the barrel includes a stop protrusion that engage lips of the protective sheath for maintaining the protective sheath on the barrel adapter in the extended position.

14. The assembly of claim 1 wherein the protective sheath includes resilient lock tab for maintaining the protective sheath in the extended position.

15. The assembly of claim 1 wherein the barrel adapter and protective sheath each have corresponding guide rails providing a longitudinal track for the barrel adapter to slide within the sheath and to provide axial alignment.

16. The assembly of claim 1 wherein the release member is integrally formed with the barrel adapter forming a syringe having a plunger, the release member having an arm having a proximal end attached to a first end of the barrel adapter and a distal end having a nub for engagement with the attachment member and a spring member adjacent the proximal end for allowing the arm to resile.

17. A one-hand releasable safety adapter assembly comprising:

an adapter including a first end having an attachment base and a second end having an elastic spring member extending therefrom;

an elastic band attached to the pair of interior fingers of the protective sheath, the elastic band is a single continuous member having an engagement portion attached to a pair of extended loops; and the engagement portion fits over a needle of a syringe mounted therein and each loop attaches to the pair of interior fingers;

a protective sheath having an aperture for receiving the adapter therein;

a release member provided by the adapter and releasably attached to the protective sheath so that the spring member is under tension; and a standard size medical device mounted to the attachment base providing the adapter assembly wherein the assembly may be held in a single hand while providing for manipulation of the release member with said hand in order to release the protective sheath and propel the protective sheath from a retracted position to an extended position.

18. The adapter assembly of claim 17 wherein the medical device includes a syringe.

19. The adapter assembly of claim 17 wherein the medical device is a standard 1½ inch syringe.

20. The adapter assembly of claim 17 wherein the medical device includes a vacuum tube.

21. The adapter assembly of claim 17 wherein the medical device includes a catheter.

22. The adapter assembly of claim 17 wherein the spring member is an elastic member that is stretched between the first end and second end in order to create sufficient force to propel the protective sheath to the extended position when the protective sheath is released from the release member.

23. The adapter assembly of claim 17 further comprising a pair of release members each having a tab engaged with a pair of apertures formed in the protective sheath and the elastic member is attached to an interior of the protective sheath.

24. The adapter assembly of claim 23 wherein the elastic member includes a first end attached to the interior finger and an engagement portion for receiving the second end and upon insertion of the adapter within the protective sheath the second end of the adapter moves away from the interior finger and stretches the elastic member therebetween until the release member engages a gripping member at the second end of the protective sheath to retain the protective sheath in a retracted position with the elastic member under tension.

25. The adapter assembly of claim 23 wherein the engagement portion is formed by a second end of the elastic member.

26. The adapter assembly of claim 23 wherein the engagement portion is formed approximately midway between the first end and a second end of the elastic member.

27. The adapter assembly of claim 26 wherein the engagement portion includes a cylindrical hub formed within the elastic member having a loop on each side providing the first and second ends.

28. The adapter assembly of claim 26 wherein the elastic member is a band and the engagement portion includes the two parallel sides of the band intermediate the first end and a second end of the band.

29. The adapter assembly of claim 26 wherein the second end of the adapter includes a notch for engaging the sides of the band.

30. The adapter assembly of claim 29 wherein the sides form a cylindrical hub having a loop on each side providing the first end and a second end of the band.

* * * * *